United States Patent
Barnes (10) Patent No.: US 8,430,812 B2
(45) Date of Patent: Apr. 30, 2013

(54) SURGICAL ACCESS ASSEMBLY

(75) Inventor: Andrew L. Barnes, Naugatuck, CT (US)

(73) Assignee: Covidien LP, Mansfield, MA (US)

(*) Notice: Subject to any disclaimer, the term of this patent is extended or adjusted under 35 U.S.C. 154(b) by 123 days.

(21) Appl. No.: 12/895,893

(22) Filed: Oct. 1, 2010

(65) Prior Publication Data

US 2011/0082344 A1   Apr. 7, 2011

Related U.S. Application Data

(60) Provisional application No. 61/248,510, filed on Oct. 5, 2009.

(51) Int. Cl.
*A61B 1/32* (2006.01)

(52) U.S. Cl.
USPC .......................................... 600/205; 600/208

(58) Field of Classification Search .......... 600/201–246; 604/167.03–167.05
See application file for complete search history.

(56) References Cited

U.S. PATENT DOCUMENTS

| | | | |
|---|---|---|---|
| 4,000,739 A | | 1/1977 | Stevens |
| 4,130,113 A | * | 12/1978 | Graham ..................... 600/224 |
| 4,610,665 A | | 9/1986 | Matsumoto et al. |
| 4,673,393 A | | 6/1987 | Suzuki et al. |
| 4,798,594 A | | 1/1989 | Hillstead |
| 4,943,280 A | | 7/1990 | Lander |
| 5,000,745 A | | 3/1991 | Guest et al. |
| 5,176,652 A | | 1/1993 | Littrell |
| 5,197,955 A | | 3/1993 | Stephens et al. |
| 5,211,633 A | | 5/1993 | Stouder et al. |
| 5,312,363 A | | 5/1994 | Ryan et al. |
| 5,389,081 A | | 2/1995 | Castro |
| 5,460,615 A | | 10/1995 | Storz |
| 5,478,318 A | * | 12/1995 | Yoon ........................ 604/167.05 |
| 5,549,565 A | | 8/1996 | Ryan et al. |
| 5,603,702 A | | 2/1997 | Smith et al. |
| 5,681,314 A | * | 10/1997 | Derouin et al. .................. 606/79 |
| 5,743,884 A | | 4/1998 | Hasson et al. |

(Continued)

FOREIGN PATENT DOCUMENTS

| | | |
|---|---|---|
| EP | 1707133 | 10/2006 |
| EP | 2226023 | 9/2010 |
| WO | WO 2005/097234 | 10/2005 |

OTHER PUBLICATIONS

European Search Report for corresponding EP 10251740 date of mailing is Feb. 1, 2011 (3 pages).

(Continued)

*Primary Examiner* — Jan Christopher Merene (57) ABSTRACT

A surgical access assembly for use during a surgical procedure includes a housing, an access member extending distally from the housing and being dimensioned for positioning within tissue and a seal assembly disposed within the housing. The seal assembly includes first and second seal components operatively coupled to each other. Each of the first and second seal components includes respective seal members defining a respective passage for passage of a surgical object. The first seal component is adapted for rotational movement about the longitudinal axis and relative to the second seal component. The first seal component may be capable of relative rotation between a first position, in which the passages of the first and second seal members are in substantial longitudinal alignment, and a second position in which the passages of the first and second seal members are radially offset to inhibit the communication of fluid through the seal assembly.

8 Claims, 5 Drawing Sheets

U.S. PATENT DOCUMENTS

| | | | |
|---|---|---|---|
| 5,807,338 A | 9/1998 | Smith et al. | |
| 5,947,954 A * | 9/1999 | Bonaldo | 604/533 |
| 6,033,426 A | 3/2000 | Kaji | |
| 6,520,939 B2 | 2/2003 | LaFontaine | |
| 6,551,282 B1 | 4/2003 | Exline et al. | |
| 6,551,283 B1 | 4/2003 | Guo et al. | |
| 6,595,946 B1 | 7/2003 | Pasqualucci | |
| 6,632,200 B2 | 10/2003 | Guo et al. | |
| 6,702,787 B2 | 3/2004 | Pasqualucci et al. | |
| 6,923,783 B2 | 8/2005 | Pasqualucci | |
| 7,081,106 B1 | 7/2006 | Guo et al. | |
| 7,083,626 B2 | 8/2006 | Hart et al. | |
| 7,153,319 B1 | 12/2006 | Haberland et al. | |
| 7,165,568 B2 * | 1/2007 | Kessell et al. | 137/68.3 |
| 7,169,130 B2 | 1/2007 | Exline et al. | |
| D537,941 S | 3/2007 | Haberland et al. | |
| D545,964 S | 7/2007 | Blanco | |
| 7,244,244 B2 | 7/2007 | Racenet et al. | |
| 7,322,964 B2 | 1/2008 | Pajunk et al. | |
| 7,390,317 B2 | 6/2008 | Taylor et al. | |
| 7,438,702 B2 | 10/2008 | Hart et al. | |
| 7,470,255 B2 | 12/2008 | Stearns et al. | |
| 7,559,918 B2 | 7/2009 | Pasqualucci | |
| 7,585,288 B2 | 9/2009 | Haberland et al. | |
| 7,731,695 B2 | 6/2010 | McFarlane | |
| 7,762,990 B2 | 7/2010 | Judson et al. | |
| 7,771,395 B2 | 8/2010 | Hart et al. | |
| 2003/0181858 A1 | 9/2003 | Lajtai et al. | |
| 2004/0171993 A1 * | 9/2004 | Bonaldo | 604/248 |
| 2004/0230161 A1 | 11/2004 | Zeiner | |
| 2007/0238337 A1 * | 10/2007 | Kimball et al. | 439/157 |
| 2008/0033363 A1 * | 2/2008 | Haberland et al. | 604/167.03 |
| 2008/0221607 A1 | 9/2008 | White et al. | |
| 2009/0076456 A1 | 3/2009 | Armstrong et al. | |
| 2009/0292251 A1 * | 11/2009 | Wenchell | 604/167.03 |
| 2011/0015491 A1 * | 1/2011 | Ravikumar et al. | 600/233 |

OTHER PUBLICATIONS

US 7,282,043, 10/2007, Racenet et al. (withdrawn)

* cited by examiner

SURGICAL ACCESS ASSEMBLY

CROSS-REFERENCE TO RELATED APPLICATIONS

This application claims priority to and the benefit of U.S. Provisional Application Ser. No. 61/248,510, filed Oct. 5, 2009, the entire contents of which is incorporated herein by reference.

BACKGROUND

1. Technical Field

The present disclosure relates to a surgical access assembly. More particularly, the present disclosure relates to a surgical access assembly including a seal assembly with seal components adapted for relative rotational movement to assist in establishing a seal about a surgical object.

2. Description of the Related Art

Minimally invasive surgical procedures including endoscopic, arthroscopic, and laparoscopic procedures permit surgery to be performed on organs, tissues, and vessels far removed from an opening within the tissue. These procedures generally require that any instrumentation inserted into the body be sealed, e.g., provisions may be made to ensure that gases and/or liquids do not enter or exit the body through the incision as, for example, in surgical procedures utilizing insufflating or irrigating fluids. These procedures typically employ surgical instruments which are introduced into the body through a cannula. The cannula has a seal associated therewith. The seal is intended to form a substantially fluid tight seal about the instrument to preserve the integrity of the established surgical site.

Seals may be limited by their ability to sustain a seal when a smaller surgical instrument is moved off-axis relative to a central axis of the cannula. Seals may also be limited by their ability to sustain their integrity when the surgical instrument is angulated. Such extreme ranges of motion of smaller diameter surgical instruments within the cannula can create a "cat eye" or crescent shaped gap in the seal that can result in a loss of seal integrity. This difficulty in maintaining seal integrity is increased when sutures are also present alongside of the surgical instrument. Additional problems include the flexibility of the seal in maintaining its integrity when both small diameter and large diameter surgical instruments are used.

SUMMARY

Accordingly, a surgical access assembly for use during a surgical procedure includes a housing, an access member extending distally from the housing and being dimensioned for positioning within tissue and a seal assembly disposed within the housing. The seal assembly includes first and second seal components operatively coupled to each other. Each of the first and second seal components includes respective passages for passage of a surgical object. The first seal component is adapted for rotational movement about the longitudinal axis and relative to the second seal component. The first seal component may be capable of relative rotation between a first position, in which the passages of the first and second seal members are in substantial longitudinal alignment, and a second position in which the passages of the first and second seal members are radially offset to inhibit the communication of fluid through the seal assembly.

The seal members each may include a slit which defines the passage. Each of the first and second seal components may include an outer segment and an inner segment depending radially inwardly from the outer segment. The outer segment of the second seal component may include a peripheral wall defining an internal boundary. The first seal component may be at least partially disposed within the internal boundary defined by the peripheral wall of the second seal component.

The first seal component may include an O-ring configured to form a seal within a surface of the housing. The first seal component may include at least one structure configured to facilitate rotational movement of the first seal component. The at least one structure may includes one or more posts extending orthogonally from a proximal surface of the first seal component. The posts are dimensioned and positioned to be engaged by a clinician. The first seal component may include one of an annular recess and an annular rib, and the second seal component may include the other of the annular recess and the annular rib. The annular recess is dimensioned to at least partially accommodate the annular rib when the first and second seal components are mounted relative to each other.

A method of performing a surgical procedure is provided. The method includes the steps of:

- accessing an underlying surgical site with a surgical access assembly, the surgical access assembly defining a longitudinal passageway therethrough and having first and second seal components respectively including first and second seal members, each of the first and second seal members defining a passage for passage of a surgical object;
- introducing fluids into the surgical site to expand the surgical site;
- advancing a surgical object through the surgical access assembly and through the passages of the first and second seal components;
- performing a surgical procedure with the surgical object;
- removing the surgical object; and
- rotating the first seal component relative to the second seal component to position the passages of the first and second seal component in radially offset relation to thereby substantially minimize passage of fluid from the surgical site and through the access device. The step of rotating may be performed prior to, during, or subsequent to the step of performing the surgical procedure.

BRIEF DESCRIPTION OF THE DRAWINGS

Various embodiments of the present disclosure are described herein with reference to the drawings wherein.

DETAILED DESCRIPTION

In the drawings and in the description which follows, in which like references numerals identify similar or identical elements, the term "proximal" should be understood to refer to the end of the disclosed surgical access assembly, or any component thereof that is closest to a practitioner during use, while the term "distal" should be understood as referring to the end that is farthest from the practitioner during use. Additionally, the term "surgical object" should be understood to include any surgical object or instrument that may be employed during the course of surgical procedure, including but not being limited to an obturator, a surgical stapling device, or the like; the term "filament" should be understood to refer to any elongate member suitable for the intended purpose of joining tissue, including but not limited to sutures, ligatures, and surgical tape; and the term "tissue" should be understood to refer to any bodily tissue, including but not limited to skin, fascia, ligaments, tendons, muscle, and bone.

Figure 1:
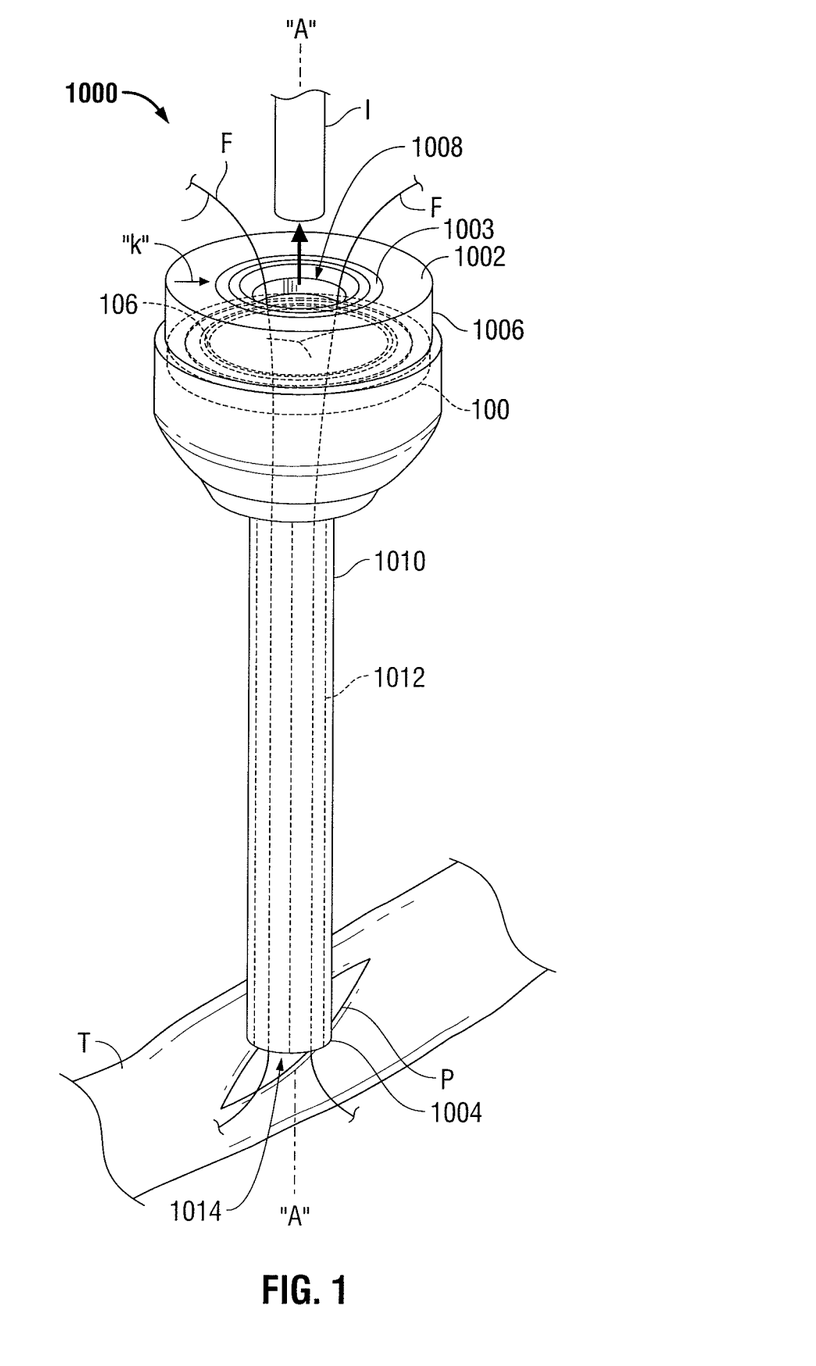
FIG. 1 is a perspective view of a surgical access assembly in accordance with an embodiment of the present disclosure.

With reference to FIG. 1, a surgical access assembly configured for use with a seal assembly 100 according to an embodiment of the present disclosure is shown designated 1000. Surgical access assembly 1000 includes proximal and distal ends 1002 and 1004 respectively. A housing 1006 of suitable proportion is located at the proximal end 1002. More particularly, the housing 1006 is configured and dimensioned to receive of one or more surgical sutures or filaments "F" and/or a surgical object, or objects "I." To this end, housing 1006 includes an opening 1008 of suitable proportion. Housing 1006 is also configured and dimensioned to accommodate seal assembly 100. An access member 1010 extends distally from the housing 1006 and is dimensioned for positioning with a percutaneous access point "P" formed in a patient's tissue "T", e.g., a patient's knee or shoulder. The access member 1010 defines a passageway 1012 (shown in phantom) that extends longitudinally through the access member 1010 and along a longitudinal axis "A." The passageway 1012 is in substantial alignment with the opening 1008. The passageway 1012 is configured and dimensioned for the internal receipt of one or more surgical filaments "F" and/or a surgical object, or objects "I." The access member 1010 defines an opening 1014 at the distal end 1004 to allow the surgical filaments "F" and the surgical object "I" to pass therethrough.

Figure 2:
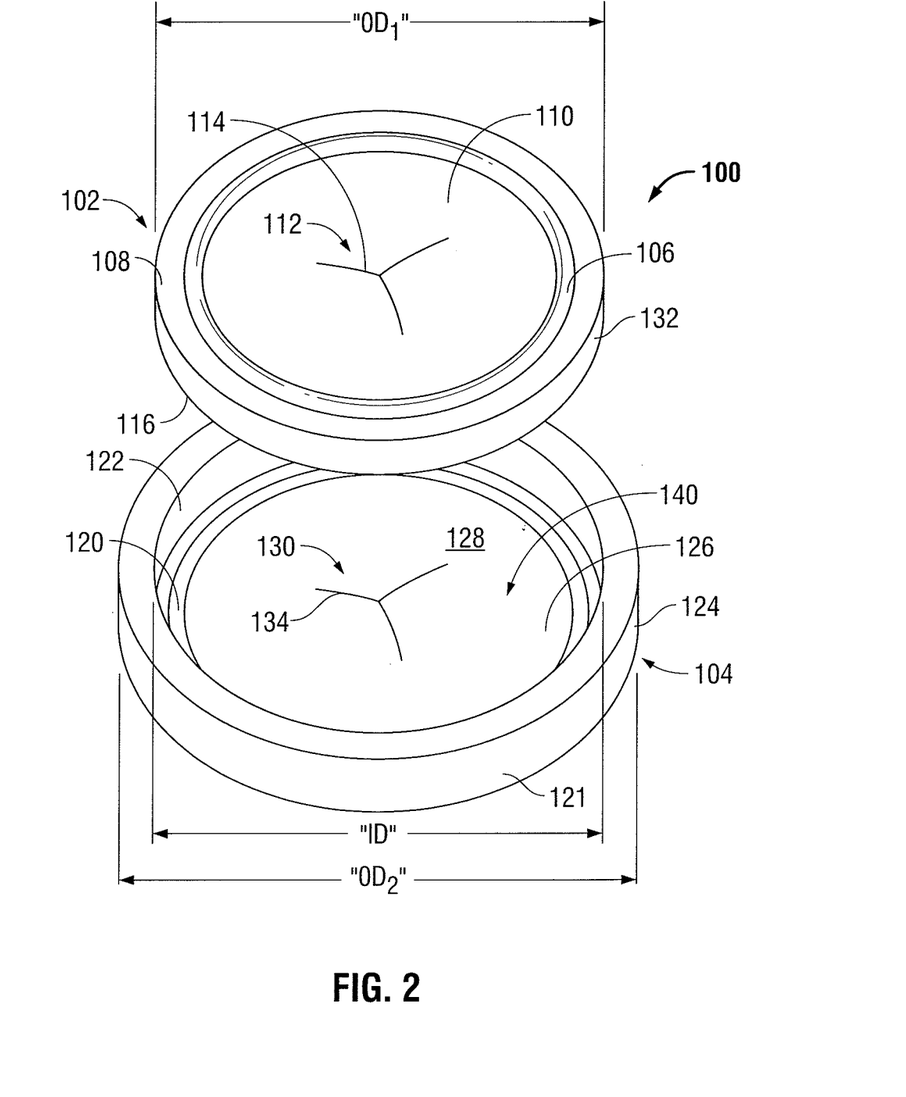
FIG. 2 is an exploded perspective view of the first and second seal components of the access assembly depicted of FIG. 1.

With reference now to FIG. 2, the seal assembly 100 will be discussed. The seal assembly 100 includes at least two seal components 102, 104 that are assembled in a manner that provides a double layer rotational seal. The seal components 102, 104 may be formed of any suitable biocompatible and at least semi-resilient material, and may be formed through any suitable method of manufacture, including but not limited to molding, casting, and electrical discharge machining (EDM). Examples of suitable materials include, but are not limited to elastomeric materials such as natural rubber, synthetic polyisoprene, butyl rubber, halogenated butyl rubbers, polybutadiene, styrene-butadiene rubber, nitrile rubber, hydrogenated nitrile rubbers, chloroprene rubber, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoplastic elastomers, thermoplastic vulcanizers, thermoplastic polyurethane, thermoplastic olefins, resilin, elastin, and polysulfide rubber. Forming the seal components 102, 104 from such materials permits the seal components 102, 104 to resiliently accommodate the insertion, manipulation, and removal of the surgical filaments "F", as well as surgical objects "I" that may vary in size.

Figure 4:
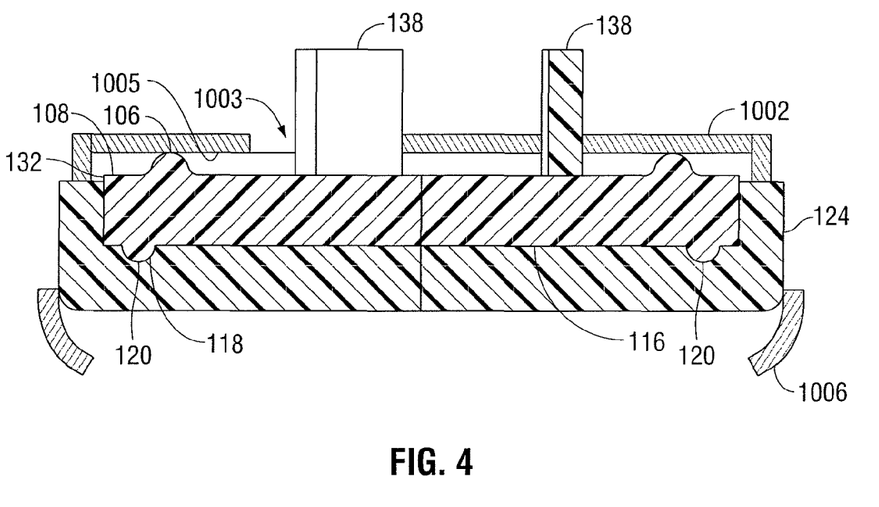
FIG. 4 is a side cross-sectional view illustrating the first and second seal components of FIG. 3 in an assembled condition within the housing of the access assembly.

Seal component 102 includes a generally circular configuration having an outer diameter "$OD_1$" that allows seal component 102 to securely and movably couple to seal component 104. With this purpose in mind, seal components 102 and 104, or components associated therewith may be coated with or made from a material that is relatively slick (e.g., PTFE). Seal component 102 includes respective proximal and distal surfaces 108 and 116 connected by an outer segment or generally circumferential sidewall 132. Side wall 132 may or may not extend in a general longitudinal direction from either of proximal and distal surfaces 108,116. In the embodiment illustrated in FIGS. 1 and 2, an O-ring 106 is operatively disposed along the proximal surface 108 of seal component 102. O-ring 106 is intended to provide a seal against an internal surface 1005 (not shown) at the proximal end 1002 of the access device 1000 (See FIG. 4). O-ring 106 may be integrally formed with seal component 102. Alternatively, O-ring 106 may be configured to seat within a groove or channel (not shown) disposed along proximal surface 108. Seal component 102 includes inner segment 110 having a passage 112 which extends through the seal component 102. Passage 112 may includes one or more slits 114, including but not limited to single-slit valves, multi-split valves, or apertures or the like configured for the intended purpose of substantially limiting the communication of fluids, e.g., saline or insufflation gas, through the seal assembly 100 when an object or instrument is inserted therethrough. In the embodiment illustrated in FIG. 2, a multi-slit valve configuration is depicted. Passage 112 of the seal member 110 extends through the seal component 102 and is normally biased towards a closed condition (see FIG. 2, for example, e.g., with the slit being substantially closed) to provide a substantially fluid-tight seal in the absence of surgical filaments "F" and/or the surgical object "I". Seal member 110 is also configured to help minimize the escape of fluid through the seal assembly 100 when the surgical filaments "F" and/or the surgical object "I" is inserted therethrough. A distal surface 116 of seal member 102 includes one or more structures 118, e.g., raised portion in the form of an annular rib 118 (as best seen in FIG. 4), configured to engage one or more corresponding structures, e.g., circular groove, recess or channel 120 (described in more detail below), proximally located on seal component 104. Rib 118 of seal component 102 engages recess 120 of seal component 104 such that seal component 102 is rotatably moveable relative to seal component 104. The rib 118 and/or recess 120 may be coated with or made from a material that is quite slippery (e.g., PTFE). While seal component 102 of the seal assembly 100 is illustrated as substantially circular in configuration, it is within the purview of the present disclosure that the seal component 102 may exhibit any suitable geometrical configuration.

With continued reference to FIG. 2, seal component 104 is shown. Seal component 104 may be operably coupled to an internal surface of the housing 1006 by any suitable known coupling and/or connecting methods (e.g., press or friction fit, adhesives, and so forth). In one embodiment, seal component 104 is secured to housing 1006 in a manner preventing rotational movement about longitudinal axis "A". Seal component 104 is configured to releasably engage seal component 102. To this end, seal component 104 includes an annular peripheral segment or wall 121 having inner and outer circumferential sidewalls, 122, 124, respectively, defining respective inner and outer diameters "ID" and "$OD_2$." Inner diameter "ID" of seal component 104 is dimensioned and configured to releasably and movably engage seal component 102 such that seal component 102 is rotatable relative to seal component 104. To this end, the inner diameter "ID" of seal component 104 is greater than the $OD_1$ of seal component 102. Inner sidewall 122 extends orthogonally from an inner surface 126 defining a cavity 140 configured to receive a portion of seal component 102. As noted above, seal component 104 includes a groove, recess, or recess 120. Recess 120 extends along a periphery of the surface 126. In the embodiment illustrated in FIG. 2, recess 120 includes a generally circular configuration and is configured to releasably engage circular rib 118. Inner seal segment 128 of seal component 104 has a passage defined by one or more slits 134.

In FIGS. 1 and 2, respective passages 112, 130 of seal components 102, 104 are in substantial longitudinal alignment, e.g., the legs of slits 114, 134 of first and second seal components 102, 104 are aligned. Alternatively, inner seal segments 128 and 110 may be radially offset from each other whereby the slits 114, 134 are radially displaced as will be discussed in greater detail hereinbelow. Seal members 128, 110 of seal components 104, 102, are configured in substantially the same manner and, as a result, seal member 128 will not be described in further detail hereinafter.

Figure 3:
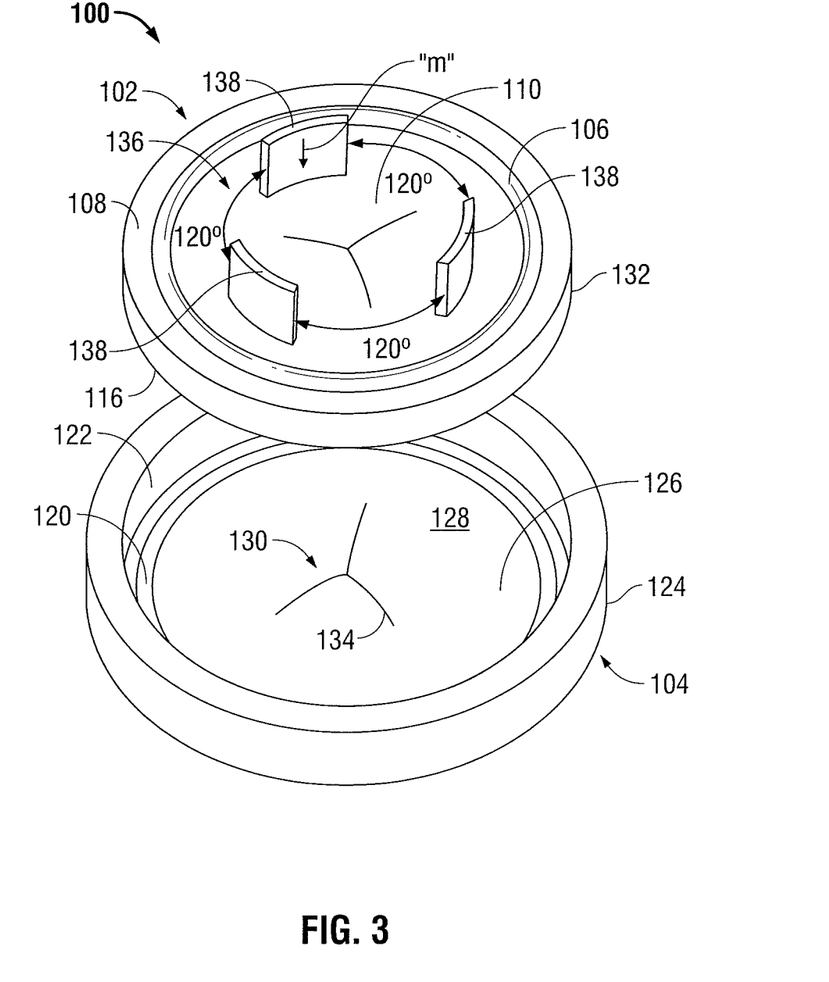
FIG. 3 is an exploded perspective view of the first and second seal components of the seal assembly in accordance with another embodiment of the present disclosure.

As noted above, seal assembly 100 includes a seal component 102 that is rotatably movable relative to seal component 104 when seal component 102 is operatively engaged with seal component 104. To this end, in an embodiment illustrated in FIGS. 3 and 4, seal component 102 may include one or more tactile structures 136 (e.g., posts, detents, ribs, slits, slots, etc.) configured to facilitate movement of seal member 102 when the seal components 102, 104 are in engagement with each other. In the embodiment illustrated in FIGS. 3 and 4, tactile structure 136 includes one or more posts 138 (3 posts are shown in the drawings) operatively disposed at predetermined locations along proximal surface 108 of seal component 102. Posts 138 extend in a generally orthogonal direction from proximal surface 108 of seal component 102. As shown in the representative drawings, posts 138 are spaced apart approximately 120° from each other. Posts 138 may extend through a corresponding annular opening 1003 (FIG. 1) in proximal end 1002 of housing 1006. Posts 138 each may extend a distance sufficient to be manually engaged by the clinician (FIG. 4).

Figure 5:
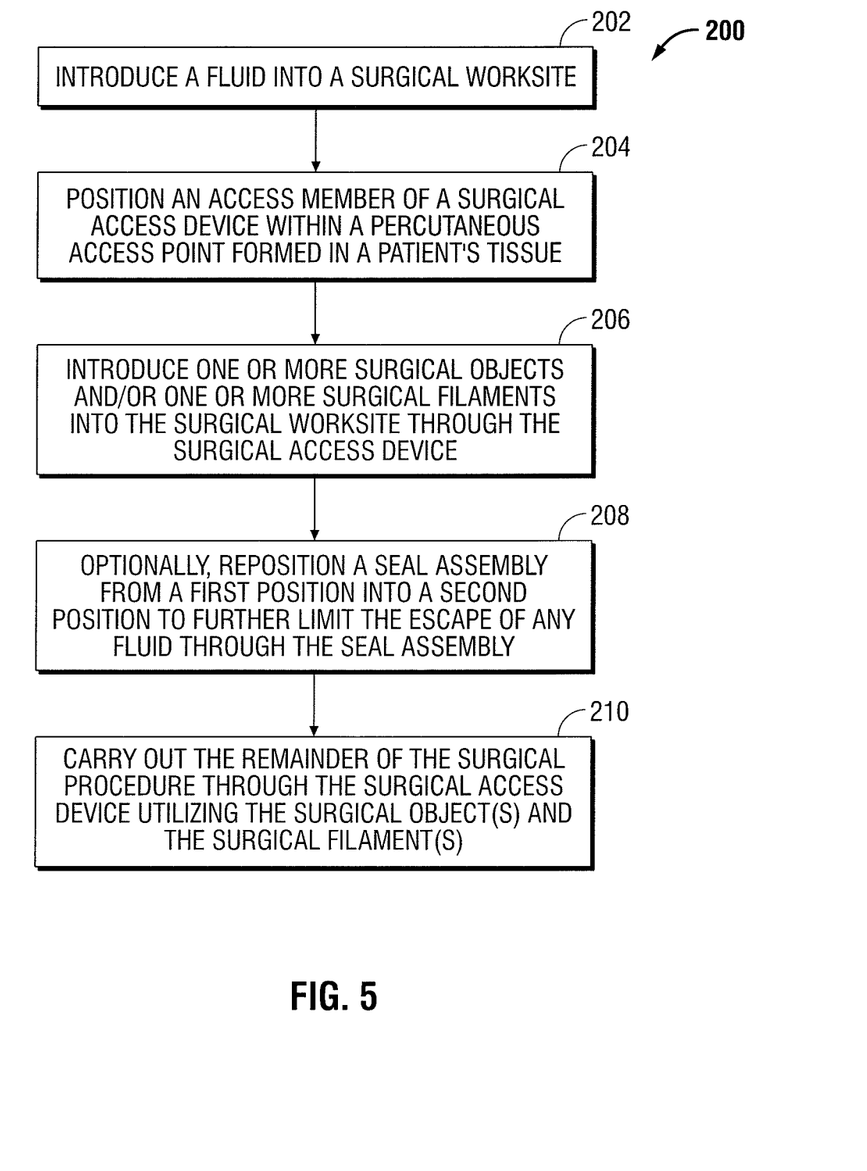
FIG. 5 is a flow chart describing a method of using the surgical access assembly of FIG. 1 during the course of a surgical procedure.

With reference to FIG. 5, a method of use of the surgical access assembly 1000 including seal assembly 100 is described in terms of use during the course of an arthroscopic procedure. Initially, a fluid, such as saline, is introduced into the surgical worksite (step 202). Thereafter, the access member 1010 is positioned within the percutaneous access point "P" formed in the patient's tissue "T" (see step 204 and FIG. 1, for example), and the surgical object "I" and/or the surgical filament "F" are introduced into the surgical worksite by passage through the housing 1006 and the access member 1010 (see step 206 and FIG. 1, for example). Either prior to the insertion of the surgical object "I" and/or the surgical filament "F" or at any other point during the course of the procedure, the practitioner may move and/or rotate (e.g., a clockwise direction) the seal component 102 (see step 208). As noted above, the seal component 102 is rotatable from a first position, seen in FIG. 2, in which the respective passages 112, 130 of the seal members 110, 128 in substantial radial alignment, into a second position, seen in FIG. 3, in which the respective passages 112, 130 of the seal members 110, 128 are radially offset from one another. Rotating the seal component 102 relative to seal component 104 interrupts and substantially closes off the path of any fluid communicated proximally through the surgical access assembly 1000 (FIG. 1) to further minimize leakage of fluid. For example, rotation of the first seal component relative to the second seal component may create a tortuous path through the seal components 102, 104 to minimize fluid leakage. Subsequently, the practitioner can manipulate the surgical object "I" and/or the surgical filament "F" through the surgical access assembly 1000 to carry out the remainder of the procedure (step 210). It is envisioned that housing 1006 and posts 138 may have cooperative visual indicia or markings which depicts when the seal components 102, 104 are rotated where the passages are in substantial alignment. Indicia may take any form. In one embodiment, the indicia is in the form of arrows "k", "m" on the proximal surface of housing 1006 and on one of posts 138, respectively (see, e.g., FIGS. 1 and 3). Other variations are also envisioned.

From the foregoing and with reference to the various figure drawings, those skilled in the art will appreciate that certain modifications can also be made to the present disclosure without departing from the scope of the same. For example, while seal assembly 100 has been described herein as being fixedly secured to housing 1006 of access device 1000, it is within the purview of the present disclosure to provide seal assembly 100 detachably mountable to the proximal end of housing 1006 and/or access device 1000. In this embodiment, seal assembly may operably couple to access device 1000 (e.g., seal component 104 includes an outer diameter $OD_2$ that is dimensioned to securely couple or engage an interior of housing 1006). Thus, the surgeon can remove seal assembly 100 from the access device 1000, for example, at any time during the surgical procedure and, similarly, mount the seal assembly 100 to the access device 1000 when desired. In addition, seal assembly 100 may be readily adapted for mounting to conventional cannulas of differing structures. The detachability of seal assembly 100 from access device 1000 or other conventional cannulas, for example, is intended to facilitate specimen removal through access device 1000.

It is contemplated that seal assembly 100 may include a tactile member (not shown) to facilitate repositioning of a portion of the seal assembly 100 between the first and second positions. The tactile member can be coupled to either the seal components 102, 104, and may be configured to depend outwardly from through an opening associated with the housing 1006 of the surgical access assembly 1000 such that the practitioner can manually manipulate the relative position of the seal components 102, 104.

It is envisioned that in embodiments of the seal assembly 100, relative movement between the seal components 102, 104 may be effectuated in any suitable manner, including but not limited to the incorporation of a mechanized assembly, such as a motor and gear set. To this end, either or both of the seal components 102, 104 may include bearings, or any other suitable structure, to assist in the relative movement of the seal components 102, 104 between the first and second positions. It is further envisioned that the seal components 102, 104 may be rotatably biased (with a spring or other suitable biasing mechanism) toward the aligned position of FIG. 2 or the non-aligned position of FIG. 3.

The access assembly may be used in conjunction with a laparoscopic surgical procedure performed, e.g., with the peritoneal cavity of the patient. In accordance with such procedures, the peritoneal cavity is insufflated and access may be established with the access assembly in a manner known in the art, e.g., with an obturator which is positioned within the access assembly and advanced to penetrate the peritoneal lining. Thereafter, the obturator may be removed leaving the access assembly 100*o* within the peritoneal body cavity. Instruments may be introduced within the access assembly and the seal components 102, 104 may be manipulated to establish a seal about the surgical instrument.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical access assembly for use during a surgical procedure, comprising:

a housing defining proximal and distal ends;

an access member extending distally from the housing and being dimensioned for positioning within tissue, the housing and the access member defining a longitudinal axis; and a seal assembly disposed within the housing, the seal assembly including first and second seal components operatively coupled to each other, each of the first and second seal components including an outer segment and an inner segment depending radially inwardly from the outer segment, the inner segments having passages dimensioned for passage of a surgical object in substantial sealed relation therewith, the outer segment of the second seal component having a peripheral wall defining an internal boundary, the first seal component being adapted for rotational movement about the longitudinal axis and relative to the second seal component, the first seal component having at least one manually manipulative member extending in at least a longitudinal direction and beyond the proximal end of the housing, and dimensioned for manipulation by the user to effect the rotational movement of the first seal component relative to the second seal component.

2. A surgical access assembly of claim 1, wherein the first seal component is at least partially disposed within the internal boundary defined by the peripheral wall of the second seal component.

3. A surgical access assembly of claim 2, wherein the first seal component is capable of relative rotation between a first position, in which the passages of the first and second seal members are in substantial longitudinal alignment, and a second position in which the passages of the first and second seal members are radially offset to inhibit the communication of fluid through the seal assembly.

4. A surgical access assembly of claim 2, wherein the first seal component is at least partially receivable by the second seal component.

5. A surgical access assembly of claim 2, wherein the seal members each include a slit, the slit defining the passage.

6. A surgical access assembly of claim 2, wherein the first seal component includes an O-ring configured to form a seal within a surface of the housing.

7. A surgical access assembly for use during a surgical procedure, comprising:

a housing defining proximal and distal ends;

an access member extending distally from the housing and being dimensioned for positioning within tissue, the housing and the access member defining a longitudinal axis; and a seal assembly disposed within the housing, the seal assembly including first and second seal components operatively coupled to each other, each of the first and second seal components including passages dimensioned for passage of a surgical object in substantial sealed relation therewith, the first seal component being adapted for rotational movement about the longitudinal axis and relative to the second seal component, the first seal component having at least one manually manipulative member extending in at least a longitudinal direction and beyond the proximal end of the housing, and dimensioned for manipulation by the user to effect the rotational movement of the first seal component relative to the second seal component, the first seal component having one of an annular recess and an annular rib, and the second seal component having the other of the annular recess and the annular rib, the annular recess dimensioned to at least partially accommodate the annular rib when the first and second seal components are mounted relative to each other.

8. A surgical access assembly for use during a surgical procedure, comprising:

a housing defining proximal and distal ends, the proximal end of the housing defining an annular opening;

an access member extending distally from the housing and being dimensioned for positioning within tissue, the housing and the access member defining a longitudinal axis; and a seal assembly disposed within the housing, the seal assembly including first and second seal components operatively coupled to each other, each of the first and second seal components including passages dimensioned for passage of a surgical object in substantial sealed relation therewith, the first seal component being adapted for rotational movement about the longitudinal axis and relative to the second seal component, the first seal component having a plurality of posts extending orthogonally from a proximal surface of the first seal component in at least a longitudinal direction, the posts dimensioned to extend through the annular opening of the housing for manipulation by the user to effect the rotational movement of the first seal component relative to the second seal component.

* * * * *